United States Patent
Muralidharan et al.

(10) Patent No.: US 8,607,618 B2
(45) Date of Patent: Dec. 17, 2013

(54) ELECTRONIC LEVEL SENSOR AND TIMER BASED FALLING HEAD SOIL PERMEAMETER

(75) Inventors: Devanatha Muralidharan, Andhra Pradesh (IN); Nanduri Purushotham Rajendra Prasad, Andhra Pradesh (IN); Rallapalli Suryanarayana Kanaka Srinivasulu, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 605 days.

(21) Appl. No.: 12/448,762

(22) PCT Filed: Dec. 26, 2007

(86) PCT No.: PCT/IN2007/000604
§ 371 (c)(1),
(2), (4) Date: Oct. 21, 2009

(87) PCT Pub. No.: WO2008/081470
PCT Pub. Date: Jul. 10, 2008

(65) Prior Publication Data
US 2010/0043532 A1    Feb. 25, 2010

(30) Foreign Application Priority Data

Jan. 3, 2007   (IN) .............................. 29/DEL/2007

(51) Int. Cl.
*G01N 15/08*   (2006.01)
(52) U.S. Cl.
USPC .............................................................. 73/38
(58) Field of Classification Search
USPC ....................................... 73/863, 38, 864.44
See application file for complete search history.

(56) References Cited

U.S. PATENT DOCUMENTS 4,099,406 A    7/1978   Fulkerson
4,348,890 A *  9/1982   Hanss ........................... 73/61.64
(Continued)

FOREIGN PATENT DOCUMENTS

GB          2027910 A  *  2/1980
WO        WO 01/90724 A1   11/2001

*Primary Examiner* — Peter Macchiarolo
*Assistant Examiner* — Tamiko Bellamy
(74) *Attorney, Agent, or Firm* — Abelman, Frayne & Schwab

(57) ABSTRACT

Determination of hydraulic properties such as porosity and permeability of soil is of paramount importance in hydrology and civil engineering. In order to achieve greater accuracy in determination of permeability of soil using falling head permeameter, the two important known constraints of human monitoring error in noting the falling water level between two selected levels and elapse time between these two levels had overcome through electronically sensing the levels between two selected points and activating the timer clock automatically by the pulses coming from senor. The precision in measurement of time lapse in $\frac{1}{100}^{th}$ of a second enables greater accuracy in estimation of permeability. Provision of perforated Teflon disc above and below the soil core facilitates in application of water uniformly over the entire surface area of soil core at top and similar way permeated water leaving the soil core uniformly without any obstruction. The use of carbon steel seamless tube while collecting soil core facilitated in undisturbed soil core recovery from desired depth section. The permeability test was conducted for various sorted sands of different size ranges and each sample was subjected to repetitive tests and elapsed time for each test was recorded from timer unit. Coefficient of Permeability was calculated for each test. The lab experiment conducted for sorted and unsorted sediments has yielded a consistent performance of Electronic level sensor and timer based falling head soil permeameter.

8 Claims, 8 Drawing Sheets

(56) References Cited

U.S. PATENT DOCUMENTS

| | | | |
|---|---|---|---|
| 4,884,436 A * | 12/1989 | Ankeny et al. | 73/38 |
| 5,672,813 A * | 9/1997 | Doherty | 73/38 |
| 6,105,418 A * | 8/2000 | Kring | 73/38 |
| 2009/0056420 A1 * | 3/2009 | Tompkins | 73/38 |

* cited by examiner

ELECTRONIC LEVEL SENSOR AND TIMER BASED FALLING HEAD SOIL PERMEAMETER

FIELD OF THE INVENTION

The present invention relates to development of an electronic level sensor and timer based falling head soil permeameter.

BACKGROUND AND PRIOR ART OF THE INVENTION

Soil permeameter is a device in the field of hydraulics, used to measure the permeability property of soil/rock. Permeability is an index of interconnectivity of pores. The coefficient of permeability is a constant of proportionality relating to the ease with which fluid passes through a porous medium. This parameter is very critical in understanding the fluid flow process in porous media and has a wide application in hydraulic engineering and fluid transport modeling studies.

Soil hydraulic conductivity has been historically measured in the laboratory, utilizing a falling or constant head of water applied to soil core samples retrieved from the field or on remolded soil samples. Laboratory measurements are often significantly at variance with in-situ field measurements because of the differing methodologies and the inherent difficulty of obtaining undisturbed soil samples. The hydraulic conductivity of soils at different depths is highly variable due to heterogeneous textural arrangement of soil particles.

It is desirable to have the capability to conduct hydraulic conductivity tests in laboratory by having the undisturbed soil in the form of a core of any desired depth above the permanent water table. Such depths may range from zero to many meters below the ground surface. In addition, it is desirable to have adequate flow capacity for maintaining flow equilibrium in a wide range of soils. Clay soils often have low permeability, whereas sandy or gravelly soils often have high permeability and, therefore, a greater accuracy is necessary in the measurement of time in case of falling head permeameter where the time reflects the permeability characteristics of soil under testing.

Prior art instruments developed for measuring hydraulic conductivity of soils generally fall into two major categories, namely- the lab measurements and in-situ field measurements. In the first type, the soil is collected from the field and subjected to permeability measurement in the lab. The second type is of measuring the permeability of soil at in-situ condition. For the first category of lab measurements, two types of permeameters are available, out of which one applies a constant head and the other a falling head. Both these types apply in principle Darcy's Law for calculation of coefficient of permeability. The second category applied for in-situ measurement of permeability utilizes various methodologies, which include electrical resistivity procedures and gas or liquid injection into the soil through penetrating probes and measuring permeability of unsaturated & saturated regime and complex analysis procedures.

The laboratory measurement of permeability is simpler, but requires collection of soil from the site, safe transportation to the lab, careful setting of lab experiment, and accuracy of measurements and reproducibility of experimental results. Among these two methods of measuring the permeability, namely the constant head has been reported, to be suitable for measuring the permeability of higher ranges, i.e. for coarser soil of more than 200 microns, while the falling head permeameter is for soils less than 200 microns having lower permeability.

The continuing physico-chemical processes ultimately disintegrate the rock into a fine soil texture and deposit in a suitable environment. In most of the semi arid environmental conditions, witnessing regular monsoon cycle, quick removal of the disintegrated rock materials and transport them to places of farther away from place of origin making them further finer particles and gets deposited as low permeable soil layers.

Reference may be made to U.S. Pat. No. 4,072,044 (Farwell et al 1976), U.S. Pat. No. 4,099,406 (Fulkerson, et al 1977) and U.S. Pat. No. 4,969,111 (Merva et al 1990) and scientific literature cited, indicating that the falling head permeameter is preferable for low permeability ranges and several errors/constraints that could affect the test results as reported are:

air trapped in sample; accuracy on measuring the elapsed time of test; uniform supply of water at the head soil core sample; disturbed soil conditions while loading the sample in apparatus; measurement error in head at beginning and at the end of test and area of specimen.

OBJECTS OF THE INVENTION

The main object of the present invention is to develop an electronic level sensor and timer based falling head soil permeameter, which obviates the drawbacks as detailed above.

Another object of present invention is to collect the soil core samples from various depths without disturbing the natural condition, of the same size of permeameter soil core chamber through coring process using the soil recovery pipe made up of seamless carbon steel tubes of various lengths by hammering process for recovering the soil as a core of particular length and depth section.

Still another object of the present invention is to have an accurate head level of start and end of test by using optical level sensors, which is of front mounting type at pre-determined heights in the burette tube.

Yet another object of present invention is to have an electronic timer unit interfaced with the level sensor to monitor the elapsed time between two pre-set levels automatically and more precisely to a level of $1/100^{th}$ of a second.

Further object of present invention is to conduct permeability test effectively by applying water uniformly over the soil surface and collecting the soil drained water without any hindrance, achieved by designing a three tubular cylinders assembly.

Still further object of the present invention is that the levels of placement of liquid level sensor can be chosen prior to the experiment by drilling a hole in the burette and fixing dome of the sensor with water leak proof condition using suitable adhesive. In the present case, the top level sensor was fixed at '0' and the bottom level sensor was fixed at 20 cm levels.

SUMMARY OF THE INVENTION

Accordingly, the present invention provides an electronic level sensor and timer based falling head soil permeameter for measuring precisely the soil permeability which comprises, a glass burette (7) with two liquid level sensors (8) fixed at 0 and 20 cm graduated positions attached to a burette stand (9) and connected to top cylinder of soil permeameter assembly through a rubber hose, the said stand further attached to an electronic timer (10) unit interfaced with the level sensor (8), the said burette (7) connected to three cylindrical copper tube chambers to receive water from burette by top chamber (5) with a perforated Teflon disc at the bottom chamber (3) and middle chamber (4), these chambers further connected to soil core recovery tubes (11), which is attached to a conical flask (2) with a discharge tube and a measuring jar (1).

In an embodiment of the present invention, the depth core soils from field sites are collected in an undisturbed condition using a carbon steel seamless tube of various lengths.

In another embodiment of the present invention, a glass burette with two liquid level sensors fixed at 0 and 20 cm graduated positions attached to a burette stand and connected to top cylinder of soil permeameter assembly through a rubber hose is used to achieve the precise detection of water level cross over at selected levels.

In a further embodiment of the present invention, the elapsed time between the liquid level-change from 0 to 20 cm is precisely measured to an accuracy of $1/100^{th}$ of a second.

In yet another embodiment of the present invention, the drained out water from the bottom cylindrical chamber is collected and a constant rate of discharge is achieved through the outlet of the conical flask during the course of experiments.

BRIEF DESCRIPTION OF THE DRAWINGS

In the drawings accompanying this specification

DETAILED DESCRIPTION OF THE INVENTION

Figure 5:
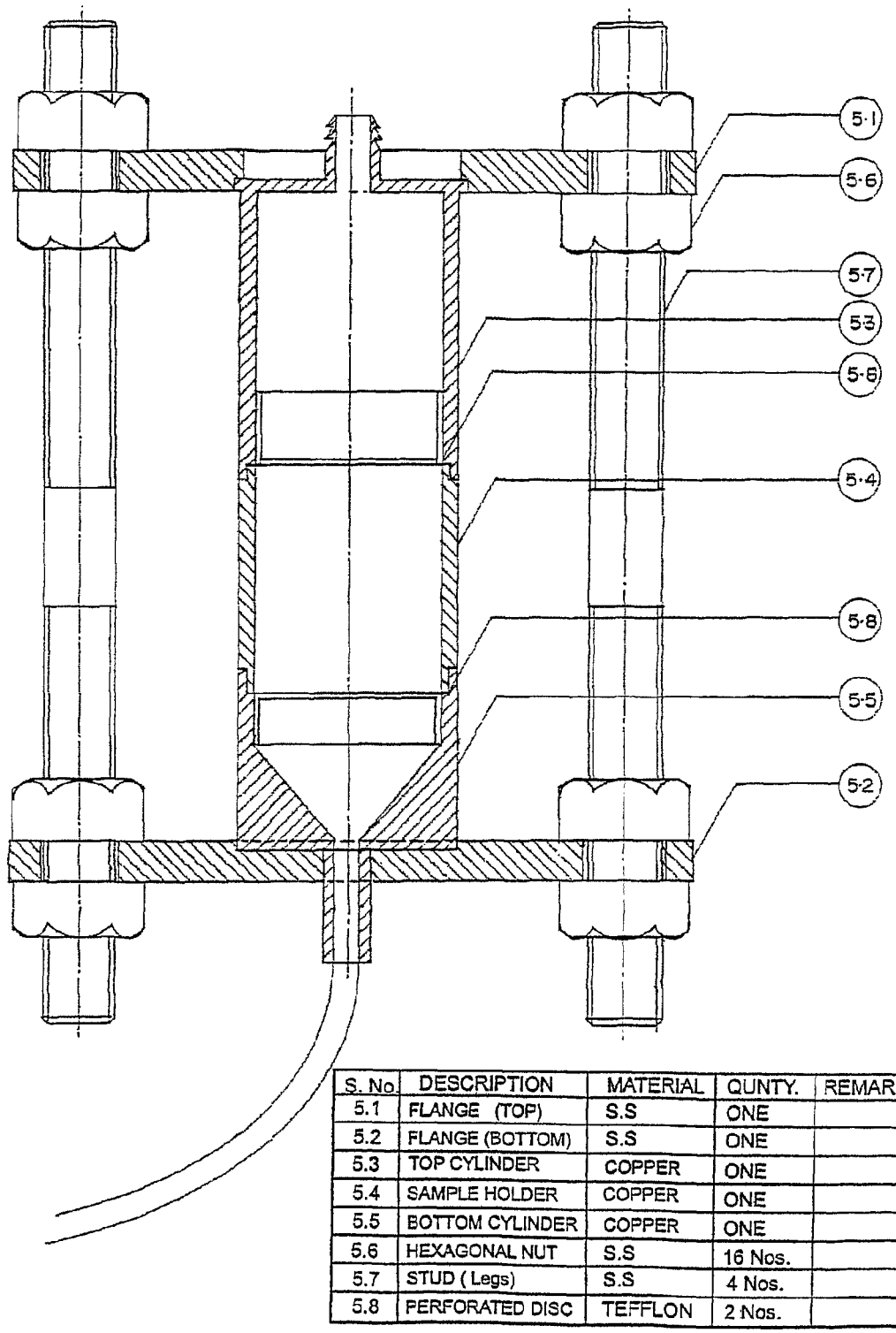
FIG. 5 represents permeameter with three cylinders assembly.
Figure 6:
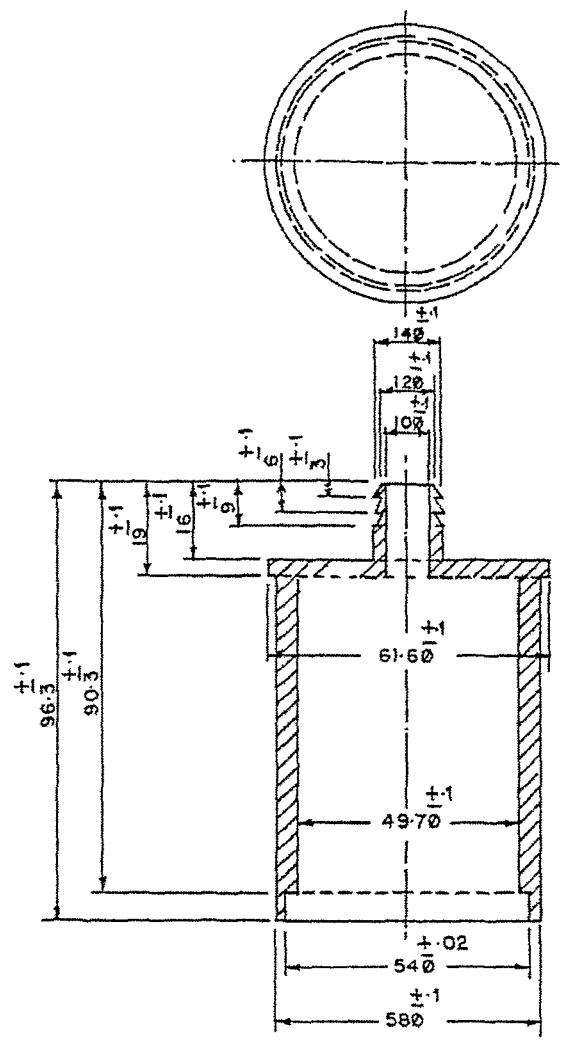
FIG. 6 represents technical specifications of top chamber, which supplies water uniformly to the soil core surface
Figure 7:
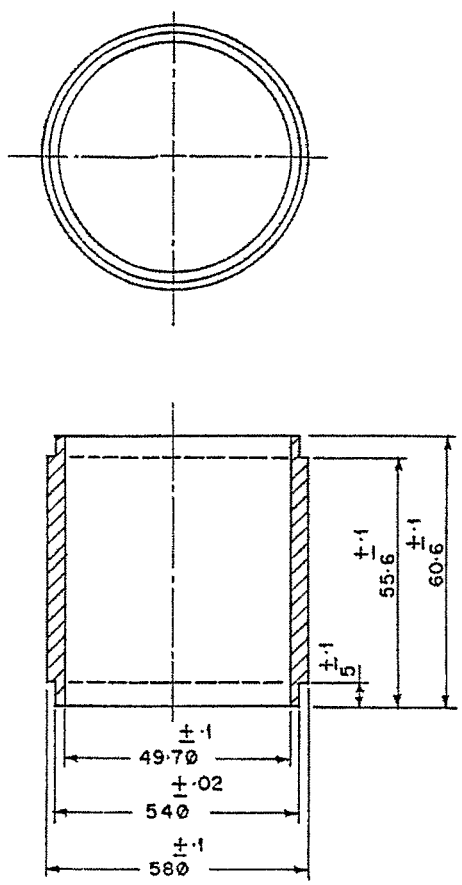
FIG. 7 represents technical specifications of middle chamber housing test soil core sample
Figure 8:
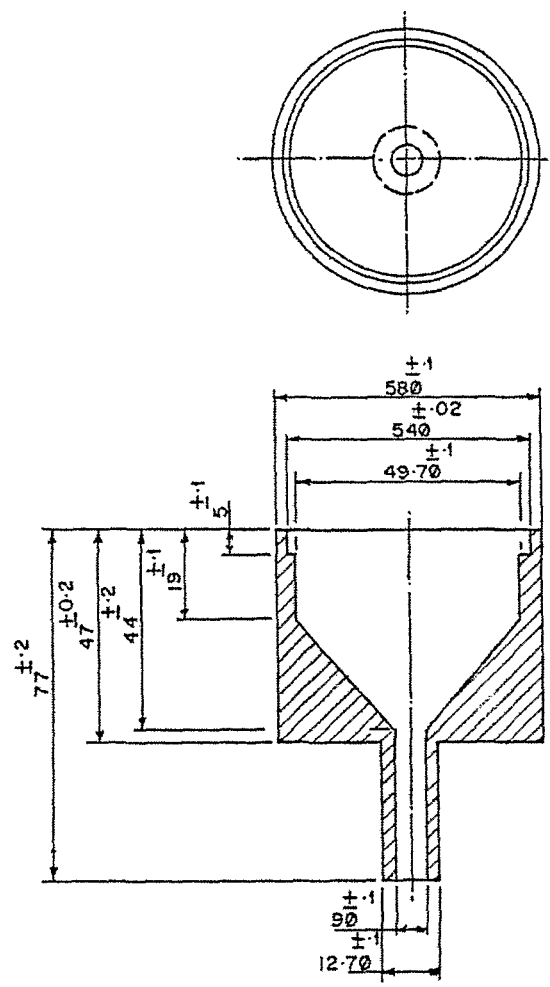
FIG. 8 represents technical specifications of bottom chamber, which collects the drained water

The present invention provides an electronic level sensor and timer based falling head soil permeameter for measuring precisely the soil permeability which comprises, soil core recovery tubes of various lengths for collecting the different depth core soils from field sites, a glass burette with two liquid level sensors fixed at 0 and 20 cm graduated positions attached to a burette stand and connected to top cylinder of soil permeameter assembly through a rubber hose to detect precisely the water level crossovers, an electronic timer unit interfaced with the level sensor to monitor the elapsed time between two preset levels automatically and more precisely to a level of $1/100^{th}$ of a second, three cylindrical copper tube chambers (FIG. 5) to receive water from burette by top chamber (FIG. 6) with a perforated Teflon disc at the bottom and middle chamber (FIG. 7) to hold the soil core with a perforated Teflon disc at bottom and bottom chamber (FIG. 8) to receive drained water with an outlet rubber hose to channel drain water, a conical flask with a discharge tube to receive the water draining through the rubber hose and a measuring jar to collect constant discharge coming out of outlet of conical flask.

In accordance with the embodiment of the present invention, an electronic level sensor and timer based falling head soil permeameter is developed for measuring precisely coefficient of permeability of soil.

In accordance with the embodiment of the present invention, a process is provided for collection of soil cores from various depths in an undisturbed condition, thus facilitating in determination of permeability to almost nearer to the natural physical condition of the soil.

In accordance with yet another embodiment of the present invention, water level crossing is detected at the chosen heights in burette by using electronic sensors and activating the timer. Two liquid level sensors fixed at '0' and '20' ml position to sense the water level crossing at these two fixed intervals and produce a pulse to the timer. The sensor uses an Opto-Schmitt trigger and principle of total internal reflection. An integral LED and photo-sensor are so arranged that when a liquid does not cover the sensor, a light path is established between them. These two components are housed in a polysulphone body for compatibility with any liquid. Total absence of any moving part in the sensor ensures high reliability even in fast cycling applications. The liquid level sensor used incorporates the principle of total internal reflection. An integral LED and photo-sensor are so arranged that when a liquid does not cover the sensor, a light path is established between them. LED and Opto-Schmitt chips are sealed into the base of a clear plastic dome in such a position that light normally totally internally reflected from the dome boundary to the Opto-Schmitt. When liquid covers the dome, the change in the refractive index occurs at the boundary and some of the light escapes into the liquid, thus less light reaches the Opto-Schmitt, which thus turns off. Direct current supply of 5 Volts is required to power the output amplifier and 30-50 mA is for the operation of internal Light Emitting Diode (LED), which is obtained by using a single current limiting resistor. The output from these two sensors is given to the interface circuit embedded in timer unit.

Sensor 1 and Sensor 2 are mounted on the burette as shown in the diagram at 0 and 20 cm mark. The counting in the electronic timer is initiated by the output of the Sensor 1 and later on the counting is stopped by the output of the Sensor 2.

In still another embodiment of the present invention a Borosil glass burette of 10 mm dia fitted with optical sensors at '0' and '20' cm levels with a facility of controlling the flow through a knob at the bottom and end tip of the burette which is connected to the top chamber through a rubber hose tightly to avoid the air entry for monitoring falling head.

In accordance with the further embodiment of the present invention, an electronic timer is provided to receive signals from the level sensors and to register the elapsed time taken to a level of $1/100^{th}$ of a second for water to cross between chosen two preset levels. The electronic timer is used here for the function of a stopwatch. An interface circuit is used here to take the input from the sensors and initiate as well stop the counting of the electronic timer. The interface circuit consists of all CMOS ICs. The electronic timer is also a CMOS based LCD display unit. The time is displayed in units of $1/100$ second, $1/10$ second, seconds and minutes. As the water column crosses the Sensor 1, a low-to-high level transition signal is obtained at the sensor output. This is given to a positive trigger input of a CMOS CD 4047(pin-8), used as a mono-stable multi-vibrator. The output of this mono-stable is a pulse. This pulse is given to an EX-OR gate of a CMOS CD 4030 (pin-1) as one of the input. The moment it receives the input pulse it transfers it to the output of this EX-OR gate, which in turn, is connected to the input of the electronic timer to start the counting process. The counting is instantly shown in the LCD display. The moment the water column crosses the Sensor 2, a low-to-high level transition is obtained at the sensor output. This is given to a positive trigger input of a second CMOS CD 4047(pin-8), used as a mono-stable multi-vibrator. The output of this mono-stable is a pulse, which is given to the second input of the EX-OR(pin-2) gate. This is instantly transferred to the output, which in turn is connected to the electronic timer, to stop the counting process and to display the total time taken for the water column of 20 ml, which is preset. The second CMOS CD 4047 (pin-10) output is connected to a buzzer circuit. The buzzer gives the tone output to indicate to the operator that the counting is over on the electronic timer. The power supply to CMOS ICs and the Electronic timer is derived from the Regulator IC 7805, giving a constant 5 Volt supply. The instrument runs on the 230 Volt line supply, hence a step-down transformer and a rectifier is used in the front end of the 5 volt regulator.

In accordance with a further embodiment of the present invention, a design is evolved facilitating to house soil core collected from the field in the middle chamber and fitting the same with top chamber of water supply and bottom chamber for collecting the drain water with provision of perforated Teflon discs above and below of soil chamber for application of water uniformly at top surface of soil core and collecting permeated water uniformly draining from the bottom of soil core.

Figure 1:
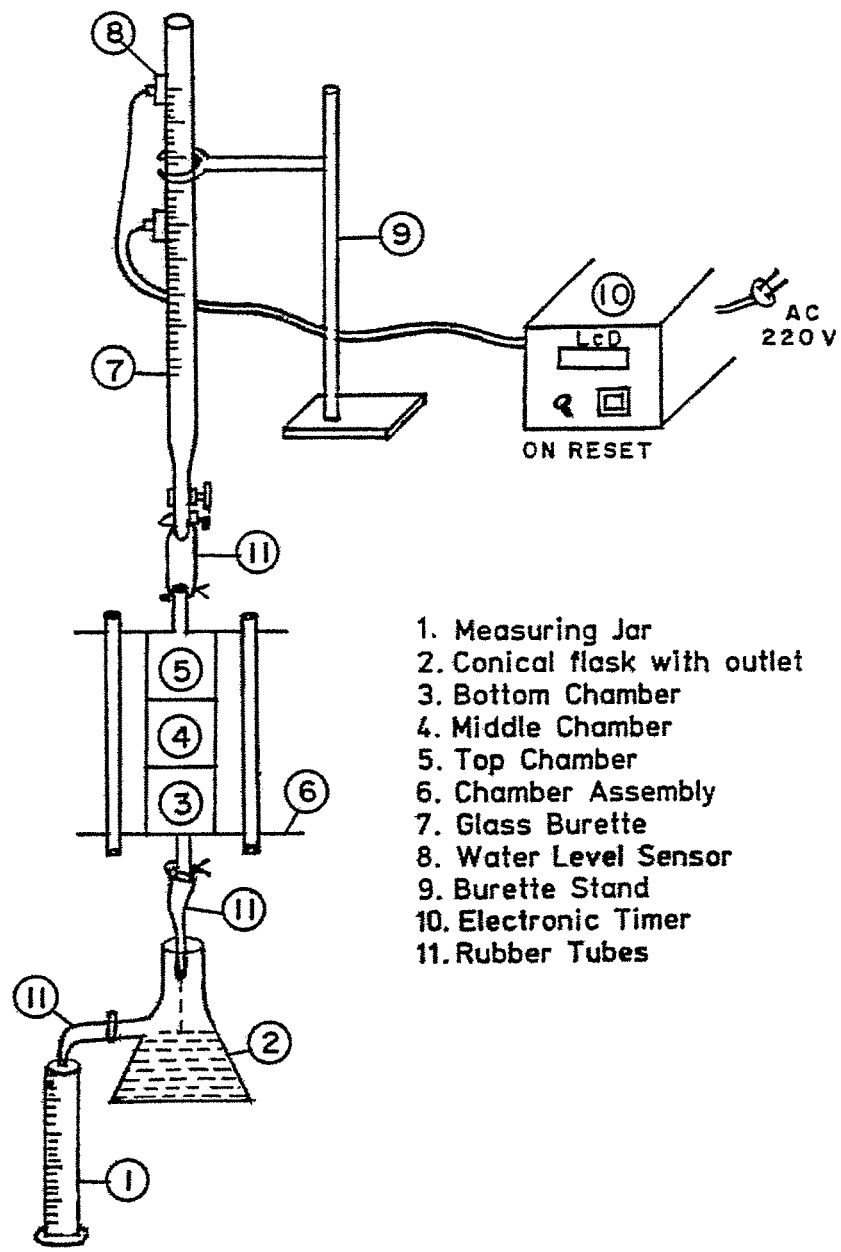
FIG. 1 represents complete setup of an Electronic level sensor and timer based falling head soil permeameter

The present invention of Electronic level sensor and timer based falling head soil permeameter setup is schematically shown in FIG. 1.

Figure 2:
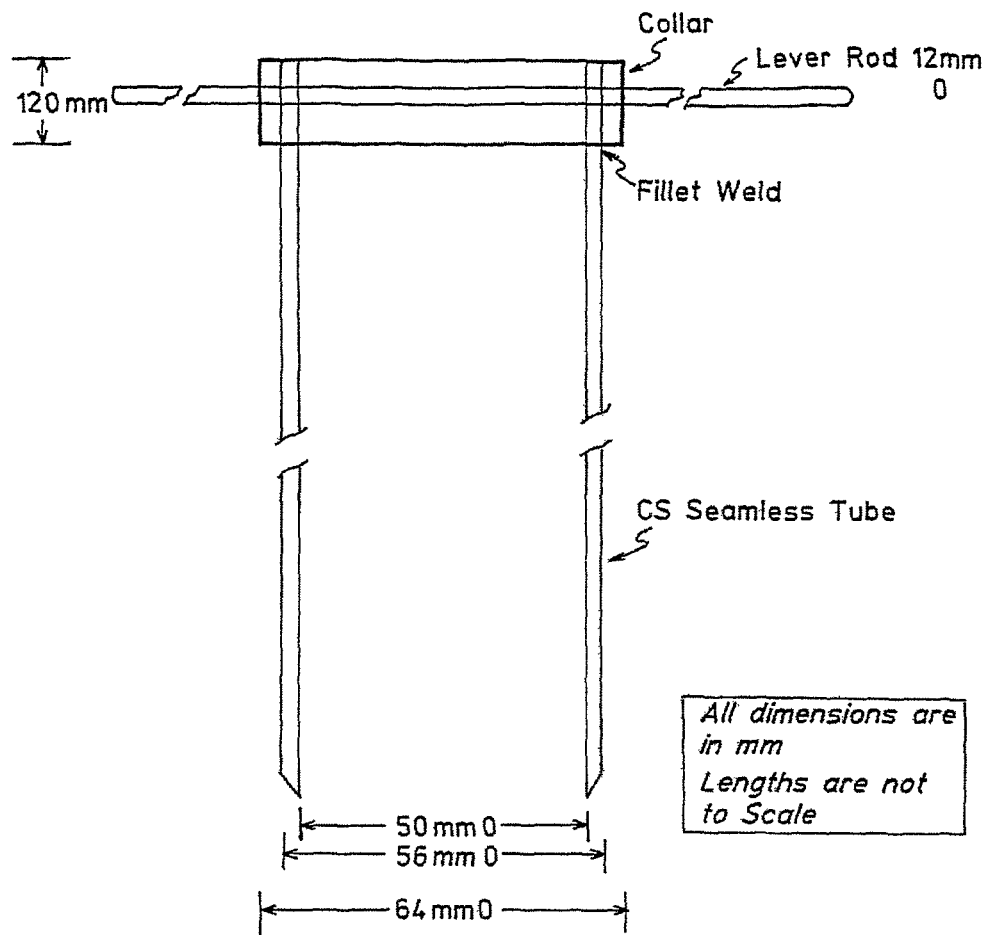
FIG. 2 represents technical specifications of soil core recovery pipes

The first step of the process is to collect soil core samples from different depths using carbon steel seamless tubes of various lengths used as per technical specifications mentioned in FIG. 2. The tubes are marked with desired sampling interval of 5 cms and driven into soil by hammering process and soil cores of various depth ranges are retrieved from inner part of the tube and marked with an arrow indicating top end of the soil core and then packed in a polythene sample bag with labeling giving site name, depth range, date of collection and transported safely to the laboratory. The samples are preserved in the laboratory according to site numbers and arranged depth wise and due care being taken to prevent disturbance to the core and as well to avoid direct sunlight falling on sample bags. The soil cores of various depth ranges of a particular site are taken for permeability test using the present invention. Each core sample is taken out from polythene bag and measured for its length and inserted in to middle chamber and then dressed at top and bottom with a knife for leveling up to chamber length. In order to avoid movement of water through contact between the soil core wall and chamber wall, silicon grease is applied inside part of chamber wall before insertion of soil core. The middle chamber holding the soil core is fitted with top chamber and bottom chamber tightly and placed inside chamber holder assembly and obtained verticality nature of chamber assembly with respect to working bench through adjustment of nuts provided in holder assembly and spirit level. The entire assembly is placed over a foldable plastic stool with a hole at the center. The outlet of bottom chamber connected with a rubber hose passes through the hole of plastic stool to drain water in to the conical flask.

Figure 3:
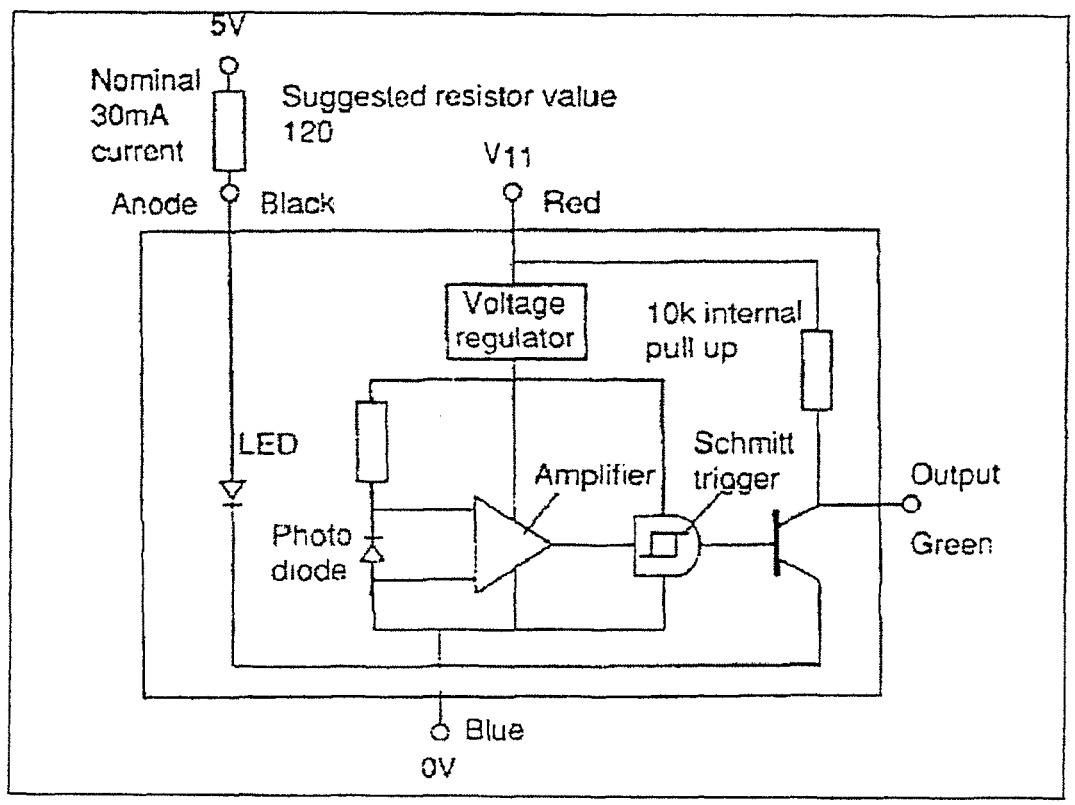
FIG. 3 represents optical sensor with front mounting type circuit diagram.

The burette with two optical sensors as per specifications mentioned in FIG. 3 is fixed at '0' and '20' Cm levels and burette assembly is clamped to a stand placed on a working bench in such a way that the outlet of burette is above inlet of the top chamber of soil core assembly. The outlet of burette is connected to inlet of top chamber through a rubber hose in such a way that connection is made airtight at both the ends. Similarly, outlet of bottom chamber is connected with a rubber hose and other end of rubber hose is let into the conical flask placed below plastic stool. The outlet of the conical flask is further connected through a rubber hose for carrying the overflow water from the conical flask to the measuring jar placed near the conical flask.

Figure 4:
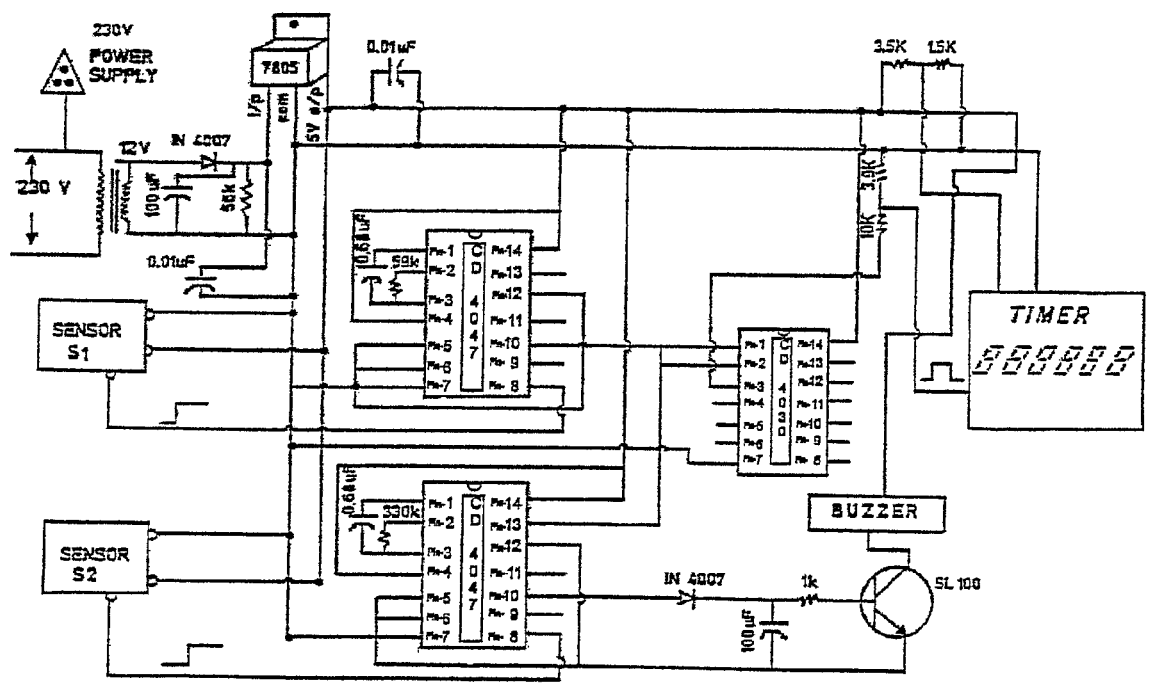
FIG. 4 represents circuit diagram of interface used for electronic timer.

The output from optical liquid level sensor is connected to a housing unit of interface circuit and timer. The interface circuit and timer unit assembly as shown in FIG. 4 is connected to power supply of 230 Volts (AC).

Once the entire setup is made, the level of conical flask output with respect to '0' mm level of the burette tube is measured in terms of height ($h_o$). De-ionized water or double distilled water is added continuously to the burette keeping full open of the control knob of burette enabling water to enter the top chamber to fill the volume and allow the water to saturate the soil core sample and start draining into the bottom chamber and comes into the conical flask. The addition of water into the burette is continued till the conical flask started draining excess water and then by adjusting outlet control knob of burette, the overflow from the conical flask remains constant, i.e., constant discharge with time. Once the level of constant outflow is achieved, the addition of water to the burette is stopped such that the water level in the burette is above the '0' mm level and the timer unit is started simultaneously. When the water level in the burette crosses the '0' mm level, timer unit starts the clock and the time count is seen on the liquid crystal diode display. As soon as the water level crossed '20' mm level, timer stops and display total time elapsed from head falling from '0' to '20' mm. The elapsed time is recorded. Water is added to the burette to have a level more than '0' mm and the timer unit is reset for making a repeat measurement. The experiment was repeated three to four times. The process is repeated for all soil core samples of a particular site, recorded and tabulated.

The calculation of coefficient of permeability (cm/sec) is done by using the following formula:

$$k = \frac{a \cdot L}{A \cdot t} \cdot \ln\frac{h_0}{h_t}$$

Where k=Coefficient of permeability (cm/sec)
a=area of burette standpipe (cm$^2$)
L=length of specimen (cm)
A=area of specimen (cm$^2$)
t=elapsed time of test (sec)
$h_0$=head at beginning (time=0) of test (cm)
$h_t$=head at end (time=t) of test (cm)

The following examples are given by way of illustration and therefore should not be construed to limit the scope of the present invention:

In order to test the function of the designed soil permeameter, sieved sand samples of various ranges of size were subjected for permeability determination. Each sample was tested number of times and time elapsed between 0-20 cm of each test was considered for permeability calculation. After ascertaining the performance of permeameter, field samples collected to a depth of 8 m from alluvium at 0.5 m interval was subjected for determination of coefficient of permeability. The various experiments conducted are briefly illustrated as examples.

River sand was sieved to various sizes of 250, 500, 1000 and 2000 microns using sieve shaker. The sieved samples were collected representing samples of having sizes between 250-499 microns, 500-999 microns, 1000-1999 microns and above 2000 microns and then subjected for permeability test using the developed apparatus.

EXAMPLE-1

The first test was carried out using the sand sample having 250-499 micron size and the test was repeated 5 times and for each test the time registered in the timer as elapsed time (t) for the head to drop or falling from '0' to '20' cm level was recorded. The height from '0' level at the beginning of the test up to the conical flask over flow level ($h_0$) was measured and recorded. The head at the end time (t) was estimated by deducting 20 cm from $h_0$ and noted as ($h_t$). The length of specimen (L) and area of the specimen (A) measured with the help of middle soil sample holder. The area of burette (a) was calculated by finding the diameter of the burette with the help of Vernier Caliper.
Area of burette (a)=0.785 cm$^2$
Length of specimen (L)=6.0 cm
Area of specimen (A)=19.002 cm$^2$
Time elapsed (t)=(Refer Table-1)
Head at beginning of test ($h_0$)=104.5 cm
Head at end of test ($h_t$)=84.5 cm

TABLE 1

| Size of sample in micron range | Electronic Timer Reading | | | Coefficient of Permeability K In cm/sec |
|---|---|---|---|---|
| | Minutes | Seconds | 1/100$^{th}$ of Seconds | |
| 250-499 | 0 | 18 | 93 | 0.0027815 |
| | 0 | 19 | 01 | 0.00276981 |
| | 0 | 19 | 10 | 0.00275676 |
| | 0 | 19 | 13 | 0.00272819 |
| | 0 | 19 | 12 | 0.00275379 |

EXAMPLE-2

The observed elapsed time and calculated Coefficient of Permeability for each test were tabulated and given in Table-2. The other parameters such as area of burette, area of specimen, length of specimen, Head at beginning and at the end being remained unchanged with that of the example 1. The same was used for estimation of coefficient of permeability.

TABLE 2

| Size of sample in micron range | Electronic Tinner Reading | | | Coefficient of Permeability K In cm/sec |
|---|---|---|---|---|
| | Minutes | Seconds | 1/100$^{th}$ of Seconds | |
| 500-999 | 0 | 15 | 34 | 0.00343247 |
| | 0 | 15 | 50 | 0.00339704 |
| | 0 | 15 | 41 | 0.00341688 |
| | 0 | 15 | 54 | 0.00338829 |
| | 0 | 15 | 19 | 0.00346637 |
| | 0 | 15 | 18 | 0.00346865 |
| | 0 | 15 | 15 | 0.00347552 |

EXAMPLE-3

The permeability test was conducted for the sand specimen of size range 1000-1999 microns by loading the specimen in middle chamber without disturbing other set up. The experiment was conducted for four times and elapsed time for each test was noted and used in the calculation. The following tabulation provides the observed elapsed time for each test and permeability evaluated.

TABLE 3

| Size of sample in micron range | Electronic Timer Reading | | | Coefficient of Permeability K In cm/sec |
|---|---|---|---|---|
| | Minutes | Seconds | 1/100$^{th}$ of Seconds | |
| 1000-1999 | 0 | 10 | 25 | 0.00513699 |
| | 0 | 10 | 22 | 0.00515207 |
| | 0 | 10 | 20 | 0.00516217 |
| | 0 | 10 | 23 | 0.00514703 |

EXAMPLE-4

In order to validate the performance of soil permeameter designed, soils were collected from natural condition. Depth samples from 0-8 m with sampling interval of 0.5 m were collected from coastal alluvium using an auguring tool. As the coastal alluvium was loose we could not collect through soil recovery pipes and therefore auguring method was adopted and depth sample interval was kept at 0.5m. The collected samples were packed carefully and brought to the lab for testing. The following Table-4 presents the time elapsed and Coefficient of Permeability determined for all the depth samples.

TABLE 4

| Depth of soil samples in cm range | Electronic Timer Reading | | | Coefficient of Permeability 'K' In cm/sec |
|---|---|---|---|---|
| | Minutes | Seconds | 1/100$^{th}$ of Seconds | |
| 0-50 | 0 | 17 | 59 | 0.002993 |
| | 0 | 17 | 41 | 0.003024 |
| 50-100 | 0 | 26 | 33 | 0.001999 |
| | 0 | 26 | 37 | 0.001997 |
| 100-150 | 0 | 13 | 56 | 0.003883 |
| | 0 | 13 | 53 | 0.003892 |
| 150-200 | 0 | 19 | 56 | 0.002692 |
| | 0 | 19 | 75 | 0.002666 |
| 200-250 | 0 | 12 | 15 | 0.004333 |
| | 0 | 12 | 19 | 0.004319 |
| 250-300 | 0 | 08 | 48 | 0.006209 |
| | 0 | 08 | 56 | 0.006151 |
| 300-350 | 0 | 34 | 75 | 0.001515 |
| | 0 | 34 | 78 | 0.001514 |
| 350-400 | 0 | 29 | 56 | 0.001781 |
| | 0 | 29 | 53 | 0.001783 |
| 400-450 | 0 | 08 | 12 | 0.006485 |
| | 0 | 08 | 09 | 0.006509 |
| 450-500 | 0 | 14 | 06 | 0.003745 |
| | 0 | 14 | 15 | 0.003721 |
| 500-550 | 0 | 19 | 23 | 0.002738 |
| | 0 | 19 | 28 | 0.002731 |
| 550-600 | 0 | 18 | 32 | 0.002874 |
| | 0 | 18 | 29 | 0.002879 |
| 600-650 | 0 | 18 | 45 | 0.002854 |
| | 0 | 18 | 39 | 0.002863 |
| 650-700 | 01 | 05 | 00 | 0.00081 |
| | 01 | 03 | 82 | 0.00082 |
| 700-750 | 01 | 38 | 05 | 0.000537 |
| | 01 | 37 | 04 | 0.000542 |
| 750-800 | 01 | 16 | 45 | 0.000792 |
| | 01 | 16 | 32 | 0.000793 |

In all the examples, repetitive measurement of Coefficient of Permeability did not vary and thus establishing the sensitivity of electronic level sensor and timer based falling head soil permeameter developed.
Advantages of the Invention:
The main advantage of the present invention is that the permeability is measured to a maximum undisturbed condition of soil; the falling head level is monitored by an electronic eye avoiding human error; the time elapsed is accurately measured by timer activated by the incoming pulse from liquid level sensor and following a fixed head level change reduces the error in estimating head at beginning ($h_0$) and head at end ($h_t$). The present invention is capable of measuring all ranges of permeability.

The main advantages of the present invention are:
1. The falling water levels are sensed precisely
2. The elapsed time between two levels is measured accurately to a level of $1/100^{th}$ of a second
3. The application of water uniformly over the entire surface area of the soil core was achieved

REFERENCES

Amoozegar, A. W. Warrick, Hydraulic Conductivity of Saturated Soils: Field Methods, Soil Science Soc AM, Madison, Wis., 1986, pp 735-770.
Ankeny et al., 1991. Method for determining Unsaturated Hydraulic Conductivity. Soil Science Society of Americal Journal. 55:467-470
ASTM, 1998. Standard method D 5126-90-Standard Guide for Comparison of Field Methods of determining hydraulic conductivity in the vadose zone, Annual Book of ASTM Standards 2001, Section 4: Construction. Vol.04.08 Soil and Rock (1):D 420-D 5779, pp. 1055-1064.
R. Allan Freeze, J. A. Cherry, Groundwater, Prentice-Hall, Inc., Enalw. Cliffs, N.J., 1979 pp 15-77.

We claim:

1. An electronic level sensor and timer-based falling head soil permeameter for measuring precisely the permeability of a soil sample, said permeameter comprising:
   a glass burette (7) having an interior, an inlet, and an output;
   upper and lower liquid level sensor assemblies (8) positioned for sensing the presence or absence of liquid in the interior of said burette, said sensors having a predetermined vertical separation from one another;
   a chamber assembly of three vertically stacked chambers, said assembly including:
   a top, vertically oriented tubular chamber (5) having an internal radius, a top chamber inlet coupled to said burette output to receive water from said burette, and a top chamber outlet;
   a middle, vertically oriented tubular chamber (4) having an internal radius which is at least approximately the same as the internal radius of the top tubular chamber, a middle chamber input coupled to receive water from said top chamber outlet, and a middle chamber outlet; wherein said middle chamber (4) holds a soil sample; and
   a bottom chamber (3) having a bottom chamber input to receive water from said middle chamber output and a bottom chamber outlet; wherein said bottom chamber (3) has an upper cylindrical portion having a radius which is at least approximately the same as the internal radius of the top tubular chamber, and a lower portion having a radius smaller than the radius of the upper cylindrical portion;
   wherein said top chamber discharges water only through said top chamber outlet;
   wherein said middle chamber discharges water only through said middle chamber outlet;
   wherein at least said top and middle chambers are made of copper;
   a first, perforated Teflon disk located in said top chamber (5) and supported on the soil sample for separating said top and middle chambers;
   a second, perforated Teflon disk seated in said upper cylindrical portion of said bottom chamber (3) for separating said middle and bottom chambers; and
   wherein said upper, middle, and bottom chambers may be disassembled from one another;
   wherein said sensor assemblies each comprise a photo sensor, an LED, and a clear plastic dome positioned relative to one another such that, when air covers the dome, light emitted by the LED is directed substantially towards the photo sensor so that the photo sensor is on; and
   positioned such that, when water covers the dome, some of the light emitted by the LED which would otherwise reach the photo sensor escapes into the liquid such that the photo sensor turns off; and
   an electronic timer unit (10) electrically coupled to said sensors in a manner such that a liquid level falling below the upper sensor assembly starts said timer unit, and such that a liquid level falling below the lower sensor assembly stops said timer.

2. The permeameter according to claim 1, wherein the depth core soils from field sites are collected in an undisturbed condition using a carbon steel seamless tube of various lengths.

3. The permeameter according to claim 1, wherein said glass burette is connected to top cylinder of soil permeameter assembly through a rubber hose to achieve the precise detection of water level cross over at selected levels.

4. The permeameter according to claim 1, wherein the elapsed time between the liquid level-change is precisely measured to an accuracy of $1/100^{th}$ of a second.

5. The permeameter according to claim 1, further comprising a conical flask (2) with a discharge tube and a measuring jar (1), wherein said conical flask is coupled to said bottom chamber outlet.

6. The permeameter according to claim 1, wherein said dome has a boundary, and wherein said photo sensor, LED, and dome are positioned relative to one another such that light emitted by said LED is internally reflected by said boundary towards said photo sensor when no liquid is present.

7. The permeameter according to claim 5, wherein the drained out water from the bottom cylindrical chamber is collected and a constant rate of discharge is achieved through the outlet of the conical flask during the course of experiments.

8. The permeameter according to claim 1, wherein said electronic timer unit comprises an Opto-Schmitt trigger circuit.

* * * * *